United States Patent [19]

Förstermann et al.

[11] 4,173,897

[45] Nov. 13, 1979

[54] METHOD OF ADJUSTING ULTRASONIC TEST SYSTEMS

[75] Inventors: Ulrich Förstermann, Sprockhövel; Hans-Peter Schäfer; Peter Möller, both of Wuppertal; Karl Ries, Mülheim; Dieter Lather, Rheurdt; Klaus-Uwe Jannsen, Lintorf, all of Fed. Rep. of Germany

[73] Assignee: Mannesmann Aktiengesellschaft, Dusseldorf, Fed. Rep. of Germany

[21] Appl. No.: 816,148

[22] Filed: Jul. 15, 1977

[30] Foreign Application Priority Data

Jul. 16, 1976 [DE] Fed. Rep. of Germany ....... 2632680

[51] Int. Cl.$^2$ ............................................. G01N 29/00
[52] U.S. Cl. ...................................... 73/609; 73/611
[58] Field of Search ................. 73/609, 611, 612, 625, 73/628, 626, 602, 619, 620; 364/507

[56] References Cited

U.S. PATENT DOCUMENTS

| 3,555,889 | 1/1971 | Weighart | 73/612 |
| 3,942,358 | 3/1976 | Pies | 73/611 |

FOREIGN PATENT DOCUMENTS 166160 10/1963 U.S.S.R. .................................. 73/611

OTHER PUBLICATIONS

B. G. W. Yee et al., Computer-Automated Ultrasonic Inspection System for Aircraft Forgings, AD 775-736, General Dynamics Technical Report AFML TA 73-194, Oct. 1973, PP1-102, P1-48 Relief On.
Young et al., Digitally Controlled Ultrasonics for Testing Steel on Line, Non-Destructive Testing, Jun. 1976, pp. 131-135.

Primary Examiner—Stephen A. Kreitman
Attorney, Agent, or Firm—Smyth, Pavitt, Siegemund, Jones & Martella

[57] ABSTRACT

An ultrasonic test system for inspection of structural material includes a test electronics for controlling a plurality of ultrasonic transmitter and receiver channels. This test electronics is operated by sequencing the system through the several channels, but the evaluating circuit is common to the receive channels. The duration of the test, timing of launching, timing of beginning receiving response signals, time and duration of looking windows for identifying and timing particular responses, and comparison data, all are operating and acquisition parameters for operating the electronics. These parameters are furnished from external sources and are programmable and exchangeable, e.g., from test to test. At least some of these parameters are updated on the basis of data as acquired during the test.

9 Claims, 1 Drawing Figure

METHOD OF ADJUSTING ULTRASONIC TEST SYSTEMS

BACKGROUND OF THE INVENTION

The present invention relates to a method of preparing automatically operating test equipment for the non-destructive testing of structural material.

Non-destructive tests of structural material are, for example, carried out by means of ultrasonics. The test electronics in the general sense includes circuitry for producing stimulating pulses for ultrasonic vibrations, and the electronics includes additional circuitry for generating and processing electrical signals produced on the basis of ultrasonic vibrations received after the launched vibrations interacted with the structural material in some fashion. Still further circuits included in the electronics processes the electrical signals to determine, for example, the transit time or other propagation times of specific signal portions (peaks, onset of peaks) and/or signal amplitudes are referenced to each other in some fashion. The signals as acquired are later evaluated, for example, in relation to stored reference data or by comparing the amplitudes of signals received and/or as produced under different conditions or after having passed through different lengths of the structural material, etc.

The processing can be carried out on the analog signals themselves or after they have been digitized. In accordance with requirements for test engineering, the test electronic must be highly individually designed. In other words, the particular equipment, that is to say, the type of transmitters and receivers, the type of signal processing, the number and design of different transmitter and receiver channels and their interconnection into a system depends to a considerable extent on the desired and required testing and on the test object, its dimensions, configuration, etc. It was found to be quite difficult to change a particular test electronic circuit in accordance with a change in these requirements. For example, a simple change such as a change in sequence of multiple sequential tests requires, in fact, redesigning and extensive intervention in the test electronic circuit.

Aside from differences in sequencing or just in the number of tests to be conducted, the electronics involved has to operate on the basis of specific parameters which are different for each of the different tests to be conducted. Of interest here is particularly test equipment in which an object is being tested from different aspects and by means of ultrasonic beams directed into and through the test object, for example, from different angles and in different directions to obtain a high resolution of the tests on one hand and to permit ascertaining of errors, flaws, defects, etc. in the structural material anywhere in the test object. Thus, each individual test is highly individualized, and the operating parameters differ individually. Such individual parameter include, for example, the period of time between the issuance of the transmitter pulse and the beginning of the period during which a meaningful response can be expected, such response being, for example, a signal that propagated through the structural material or an echo signal, i.e. test signal which was reflected by a flaw or a boundary of the object. Other parameters are the necessary gain in the receiving circuit; threshold responses to amplitudes, or transit times, etc. These parameters can all be adjusted but it is very clear that each particular and unique parameter which is needed within the test system is separately adjusted, and there must be provided at least one particular adjusting member for each parameter. There may be some sharing of system components in the equipment but the adjustment of parameters for a multi-head or multi-channel system becomes plainly a matter of multiplying the needed parameters in accordance with an increase in test head, test channels, etc. Since these parameters have to be adjusted manually it is apparent that the probability of incorrect adjustment increases with the complexity of the system, so does the time it takes to initialize and check the test system and its adjustment.

In some instances, the utilization of electronic data processing equipment has been employed in order to evaluate, for example, test results to determine whether certain limits have been exceeded, to calculate propagation times, etc. The known equipment, however, is not designed to adjust the test electronic in accordance with the operation of a processing system.

DESCRIPTION OF THE INVENTION

It is an object of the present invention to provide a new and improved method of adjusting the electronics of ultrasonic test electronics in accordance with test specific requirements.

In accordance with the preferred embodiment of the present invention, it is suggested to construct the test electronics in that the elements and components requiring variable parameter adjustment, are designed to receive signals defining the respective parameter so that upon reception of such signals the components and elements are adjusted accordingly. These signals are fed to the test electronics from an external source for parameters, whereby at least some parameters in the test electronics are modified for each new test.

Consider the following example of testing stepwise a sheet of metal. After an initial test run one has available a plurality of information signals in form of amplitude and transit or propagation times. Out of these data one can calculate the sheet thickness in terms of transit times and signal delays. That, in turn, determines the timing and duration of a looking window for a flaw echo. By checking, after each run, on the sheet thickness (detecting echos from the front and from the rear surface of the sheet), one will detect changes thereof (which in itself may be regarded as test data), and any change in sheet thickness is now used to recalculate the beginning and end of the flaw echo looking window. The test electronics includes a window generator (gating signal) which is responsive to signals for the metering of beginning and end of the window generation. These signals are the operating parameters for the generation of the window and they are furnished on the basis of the calculation as performed. The calculating facility is, thus, a source external to the test electronics which provide operating parameters to the test electronics.

The relevant test parameters can be divided into the groups, one constitutes operating parameters in a more specific sense, the other group constitutes process parameters for the acquisition of specific information involving recognition and isolation of specific portions of the ultrasonic signal as received.

The operating parameters proper are the duration and sequence of tests including here the selection of the transducers participating in a test and their respective mode of operation or even changes during a test. Other operating parameters are the relative timing of launching an ultrasonic wave, and the (subsequent) beginning of the period during which response and interaction can be received.

Acquisition parameters are the looking windows and gating signals to limit responses to selected, timed periods, such as specific periods in which particular boundary echos must occur, or periods in which echos if occurring constitute flaw echos. Other acquisition parameters are particular limits for the transit or propagation period of specific expected interaction signals, as well as limits (upper or lower) for specific amplitudes. All these parameters can be expressed in signals which, when applied to appropriate circuit elements, preset and adjust these elements in terms of operating and acquisition parameters as the case may be.

The invention permits non-destructive testing on a large scale and on line during running production involving the test object. The period for each test in the sequence is adjusted in accordance with the progress of the production.

DESCRIPTION OF THE DRAWING

While the specification concludes with claims particularly pointing out and distinctly claiming the subject matter which is regarded as the invention, it is believed that the invention, the objects and features of the invention and further objects, features and advantages thereof will be better understood from the following description taken in connection with the accompanying drawings in which:

The FIGURE illustrated in block diagram of a system in accordance with the preferred embodiment of the invention.

DETAILED DESCRIPTION OF THE DRAWING

Figure 1:
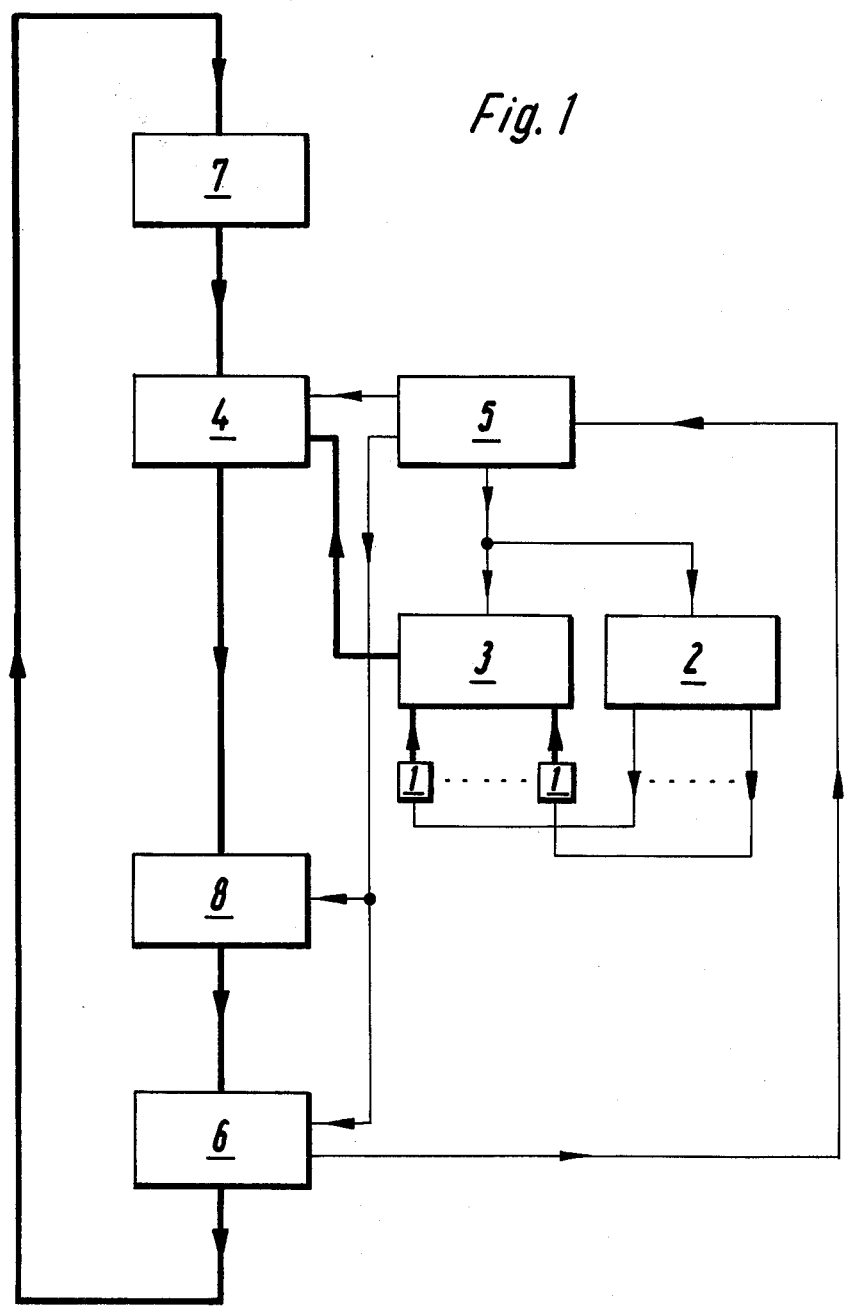

Proceeding now to the detailed description of the drawings. The FIGURE shows a plurality of transducer heads or a group of transducer heads (1) to be disposed in relation to a test object. These test heads are, for example, coupled to different portions of the test object or they are arranged so that a certain incremental portion of the test object to be tested is coupled sequentially to the various test heads. This way the incremental portion of the test object is inspected, for example, from different directions.

It is assumed that all or at least some of the transducer heads include a vibrator-oscillator capable of tranmitting ultrasonic vibrations upon being stimulated; the stimulation may, for example, result from electrical pulses so that the respective vibrator issues ultrasonic waves. These pulses propagate into the test object and interact therewith. In some instances, internal reflections and echo pulses are produced on interfaces or boundaries of the object and by flaws therein if there are any. In other instances, still involving the same object, the ultrasonic signal may travel through the test object to be received at the other end of the propagation path. In all these cases the same or another transducer head still included in the plurality of heads 1 will receive an ultrasonic signal and convert the vibration into an electrical signal for further usage.

The ultrasonic signals as so received and the electric signal generated in response thereto includes valuable information. For example, the time of arrival of the signal or of a particular portion of the signal, such as the peak amplitude, is of interest. Particularly, the time between an echo produced when the test signal entered the test object, and an echo resulting from reflection of the test signal at the opposite boundary of the object (rear wall echo) is a measure of the local thickness of the object, and the two echos are reference signals in that any echo between them must be an echo from a flaw. In the case of a flaw-produced echo the timing of the echo relative to front and rear wall echos is of interest for locating the defect. In this, as well as in other instances, the amplitude or other contour of the received signal is of informative value. All these features of the received signal yield or may yield information as to the internal state of the test object usually but not necessarily of a limited portion thereof.

In all these instances, speaking generally, each particular test can be defined as orginating with the issuance of an ultrasonic pulse followed by the reception of a response or the detection of the absence of a response. Such a test inspects usually a very limited volume portion of the test object. Generally, an extensive test program will involve the sequential coupling of the transducer or the transducers involved in one such test to different portions of that test object. Moreover, as stated above, different heads, for example, differently oriented test heads, may test the same or approximately the same incremental portion of the test object from different directions. (See, e.g., U.S. Pat. Nos. 3,868,847; 3,850,027; Ser. No. 641,916, filed Dec. 18, 1975, now U.S. Pat. No. 4,003,664; and Ser. No. 767,353, filed Feb. 1, 1977, now U.S. Pat. No. 4,131,027).

These various tests are not carried simultaneously but the various heads involved in the overall testing program may be disposed in a certain geometric relation to each other whereby different heads are coupled in any instant to a different portion of the test object. As the object moves relatively to the heads, all portions of the test object are sequentially coupled to each of the test heads or paired groups of them as involved in a particular test, while on the other hand, for each particular geometric relation (position) of the test object to all of the test heads, tests are sequentially conducted involving in each instance a different portion of the test object.

Usually, these tests cannot be conducted simultaneously because different test signals will interfere, and the responses become indistinguishable. Therefore, it is necessary to sequentially operate the various test heads, i.e., the various tests are being conducted sequentially, while the test system as a whole has a specific position to the test object and its various positions. As to each such position, a test conducted on the basis of an ultrasonic signal launched by one transducer, is regarded as a test. Running through all transducers involved, is a test cycle, i.e., a complete sequence of tests. The sequence is repeated in a different position of the system as a whole relative to the test object. Thus, a test cycle involves a sequence of tests of each test therein involves a different head or pair of heads or different operational modes of a head; for example, a head may operate as a transmitter as well as receiver in the same as well as in different tests. Moreover, for various purposes, tests may be repeated within a sequence, see e.g. Ser. No. 775,159, filed Mar. 7, 1977.

A control unit and transmitter circuit 2 furnishes the signals which control and stimulate the transducers 1 as to transmission of ultrasonic waves. Accordingly, the circuit 2 has a plurality of output channels, in the following called transmitter channels, which are individually coupled to the transducers 1 of the plurality. Unit 2 is basically a set of amplifiers or a single amplifier with different output (driver) stages and generate the needed electrical stimuli, one at a time, for a selected transducer to operate as a transmitter of an ultrasonic signal. The unit 2 is under control of a timing and control circuit 5, and receives therefrom addressing and selecting signals which are decoded by the circuit 2 for purposes of enabling a particular transmitter channel. In addition, the control unit 5 provides firing signals for the selected transducer in particular, timed relation to the selection. Thus, controller 5 selects the transducer participating in a test as a transmitter and times the launching. Timing of launching can be metered by a single timing circuit which is adjusted anew (if necessary) for each test.

The test heads 1 and particularly those or those portions thereof which will or may operate as receivers of ultrasonic signals, are connected to a receiver circuit 3 which has as many input channels as different signals are received. The circuit 3 includes one or several suitable preamplifiers as well as gates to open a selected input and receive channel for a limited period of time only. It limits broadly the period of time during which an ultrasonic vibration received by a transducer coupled to that particular receiver channel will be recognized as a signal of informative value. The particular selection of one of the receiver channels of the plurality, and the timing of a response, is made on the basis of an addressing or selecting signal furnished by the control unit 5 as well as by timing signals bearing a specific delay to the launching of a test signal by the selected transmitter channel.

The signals are received and preprocessed in the selected receiver channel and are fed to the acquisition unit 4. The unit 4 can be regarded as or implemented by a microprocessor or mini computer. This unit has basically three inputs or input channels, one of them is a common data channel or bus leading from the receiver circuit 3 (all channels) to the acquisition unit 4 and receiving sequentially a train of signals which have resulted upon receiving ultrasonic signals after having interacted with the test object following the transmission of an ultrasonic signal into the test object by one of the transmitters. Thus, the sequential selection of receiver channels operates as a time-multiplexing operation, resulting in a single data stream to acquisition unit 4. The second input for unit 4 is an address but identifying the currently selected transmitter and receive channels. The third input for unit 4 is the output of a memory or data source for the operating parameters to be used as part of the acquisition process.

The data signals from the receiver 3 constitute a more or less irregular stream of data, possibly analog data, which are applied by the circuit 3 to the unit 4 in the sequence of enabling of the individual receiver channels as per the desired test sequence. Additional sorting and discrimination is required in order to separate (de-multiplex) the individual portions of this signal train from each other.

As was already mentioned above briefly, the reference numeral 5 refers to a control circuit and timing circuit 5 which can also be described as being a programmed timing unit. As far as the acquisition and processing unit 4 is concerned, circuit 5 furnishes timing pulses and test identifying numbers. The timing pulses are related to the instances in which the controller 5 has commanded the respectively selected transmitter channel to launch an ultrasonic test pulse. The test identifying signal identifies numerically the particular test, so that the signal in the data line soon to follow can be properly associated with the particular test and with the transducers involved in the test.

As stated, the controller and timing unit 5 provides control and timing signals for the transmitter and receiver circuits 2 and 3 as well as for the processor 4. In a simple version, it is conceivable that the controller 5 simply provides a sequence of enabling signals activating one receiver channel and one transmitter channel after the other in cyclic sequence and, of course, in accordance with a fixed sequence within each cycle. However, for a more involved system as invisioned here, unit 5 includes an address and test sequence counter whose count state serves as addressing signal for the processor 4 identifying in sequence the particular test that is being conducted. Alternatively, controller 5 may furnish these test identifications and address signals to units 2, 3 and 4 in random sequence including repetition of the same test number. Moreover, different tests under different numbers may not necessarily involve entirely different heads, but the pairing may be different and the operational mode may change. Thus, the selection signals furnished by controller 5, are external signals as far as receiver and transmitter channels (3,2) are concerned, and these selection and addressing signals may vary at random, in prescribed sequence or under control of a unit 6 to be described.

The test identification number as so provided by the controller 5 is, as far as the operation of the transmitter and receiver electronics are concerned, a random or quasi-random operating parameter for the circuits 2 and 3. The controller 5 furnishes, in addition, the trigger signal for the selected transmitter channel and launch transducer. This signal bears a timed relation to the selection and constitutes another operating parameter. The controller may meter this delay by a counting process using a preset count number which may be furnished as a unique operating parameter under the test identification number. The timing and control unit 5, therefore, controls the actual conduction of the test. It includes a particular clock counter which permits metering of definite periods of time beginning, for example, on an arbitrarily selected launching time which follows, for example, the incrementing step of the test and sequence counter in the unit 5. A register in the unit 5 may hold the particular launch delay parameter as a number, and when that clock counter has reached that number, a comparator responds and causes a timing pulse to be sent to the receiver circuit 2 for purposes of launching the ultrasonic test wave. An analogous parameter is a metered delay furnished by controller 5, and determining the relative timing as to when the selection of the receiver channel to be selected is to take place. Metering the delay involves also an externally provided count number determining when the delay has been metered by a counting process. The same clock counter can be used in 5 for metering this delay.

The data acquisition facility 4 receives the particular raw data signal which the respectively enabled receiver channel has set into the data channel or bus leading to the facility 4. In addition, as outlined above, facility 4 receives from controller 5 signals being test identifying numbers. The particular acquisition facility will now, for example, determine the transit time by metering the period between a settable zero point in time, and the occurrence of particular receiver signal amplitudes in the data channel, as well as relevant delays between certain identified signal peaks. For the same test acquisition, the unit 4 may also determine the amplitude of specific portions of the data signal, and particularly, whether or not and when specific limits were exceeded. One of the main points is the isolation and identification of specific signal portions and their occurrence (or non-occurrence), which is made on the basis of generating specified looking windows or gating periods within which a particular ultrasonic response signal is to occur in order to be identified as a specific response, such as an echo from a physical boundary of the test object.

The signal in the data channel from multiplexing receiver circuit 3 may be digitized on the input side of the facility, so as to permit digital processing. The facility 4 requires for its operation reference data for making these determinations; for example, each test involving a different head or a set of test heads has to be associated with particular inherent delay; such a delay may occur, for example, on account of the specific mode of coupling the test head or heads to the test object, with or without a fluid coupler path or with differently long fluid coupler paths, etc. These delays all have to be taken into account for determining a transit time or other propagation time and differ from test to test.

For reasons above, this acquisition process involves the generation of looking windows, that is to say, certain signal paths are gated open and closed again for a limited period of time only, and additional circuit elements are specifically enabled to determined whether or not and/or to what extent the ultrasonic data signal (digitized) has a certain characteristics, e.g., whether a particular peak occurs in one period and when, and whether the signal amplitude exceeds a particular value, etc. Each test may involve different peaks, even a different number of relevant peaks, and totally different times of occurrence. Thus, unit 4 includes one or more window generators, which provide gating signals, whereby each gating signal is to begin and to end in a particular timed relation to the zero time reference point; from test to test these times differ. Thus, the window generator or generators are constructed to receive acquisition parameters in the form of count numbers, and a time-clock counting process meters the gating periods, i.e., their beginning and end by counting in relation to the zero point and by opening the gate when the beginning-of-window-parameter count has been reached, and by closing the gate when the end-of-window-time count and parameter has been reached.

The acquisition unit includes additionally circuitry to compare the or an amplitude of a signal received, e.g., during one of the gating signals with preset amplitude values which again may differ from test to test, though involving the same comparator circuitry. Examples for such equipment are shown, e.g. in application Ser. No. 816,149 filed July 15, 1977.

The several elements and components as described, operate with the aid of operating parameters such as time count numbers and amplitude limit or reference values. All these elements in unit 4 are constructed to receive these parameters as input signals for purposes of conducting the acquisition on the basis of these parameters.

In accordance with the invention method, all these acquisition parameters needed for interpreting the measuring signals are contained in a read/write store or memory 7. The store or memory 7 is addressable by the acquisition unit 4. Accessing is carried out on the basis of the test identifying number furnished by the controller 5 in the beginning of each particular test and actually prior to the conduction of each test. The store or memory may also include a particular calculating program, or micro-programs, called upon in response to the test identifying number as it is furnished at the beginning of each particular test by the controller 5. This program will begin to be executed as soon as such a test begins. The execution of that program involves setting up the electronics-acquisition unit 4 by extracting the reference data and acquisition parameters needed for evaluating the measuring signals soon to arrive from the selected receiver channel, and by distributing these parameters or making them available as function and operating parameters in the various components (comparators, window generators) that need them in order to be able to fulfill their function in the specific manner as required by the current test. As soon as controller 5 signals a new test by issuing a new test identification number, a new set of such acquisition parameters is taken from memory 7 and made available to the unit 4.

The specific test process data which results from the processing by acquisition unit 4, are accumulated in an output buffer 8 to be held therein under the current test identification number for further usage. These result-data may include the actual relative time of occurrence of signal peaks, onset of signals, occurrence or non-occurrence (plus timing) of a flaw echo whether or not amplitudes have been exceeded, etc.

This invention is not involved with the further processing of the measuring signals and result-data as such and for purposes of correlating defect detection with the detection of defects carried out in different test cycles at different times. Of relevancy here is only that the test data acquired such as the specific identification of particular amplitudes, and the determination of their particular transit times for particular tests, are being stored in the storage facility 8.

The device 6 is another processor which, in accordance with its own program determines whether or not the acquisition parameters used by the equipment, such as the location and time of the looking window, amplitudes, thresholds, etc., were, in fact, adequate and correct. As a consequence, that determination may now find that the looking window was not completely correctly placed or that for specific reasons a differently phased looking window should be used in a repeat of that test. Accordingly, the processing device 6 updates the acquisition parameters that were used in the previous test, and the result of executing this update program, may or may not demand a repeat of this test.

The device 6 will transmit to the memory 7 updated test parameters, for example, different data for the looking window, etc., and under the same sequence number, the test is repeated. Conversely, the device 6 may decide that a repeat is not desired and will issue an incrementing signal to the test number counter in controller 5 so that the next test can be conducted. A sequence of such update and test repeat operations is described by way of example in a patent application of some of us, Ser. No. 775,159, filed Mar. 7, 1977.

One can see that the update-processor 6 does not just have the last test results available, but the content of the entire buffer. Therefore, acquired data from other tests can also be drawn upon to recalculate acquisition parameters.

The data channel from processor 6 to controller 5 may, additionally, include the transfer of information needed as parameters in the controller 5. These are the delay signals (count numbers) to meter the launching time and to meter independently the instant to render the selected receive channel conductive. These are all operating parameters having to do with the actual conduction of the test, its sequencing, duration, launch time, and beginning of acquisition (receiver enabling). These parameters may be stored in a separate memory of processor 6, and are applied by that processor 6 to the controller 5 for distribution therein. The processor 6 receives the test identification number from controller 5 also for that purpose. The processor 6, therefore, performs separate functions for each test. In the beginning, it provides the operating parameters, and later processor 6 undates the acquisition parameters and updates memory 7 accordingly. In addition, processor 6 may control the sequence of the tests or modifies an otherwise regular sequence by furnishing a test identification number to controller 5 (e.g. in the case of one or several repeats) to supercede the test number counting in controller 5.

The invention is not limited to the embodiments described above but all changes and modifications thereof not constituting departures from the spirit and scope of the invention are intended to be included.

We claim:

1. In a method for ultrasonic inspection of structural material using a plurality of transmitter and receiver channels, and wherein the channels of the plurality are operated in steps, comprising:

sequentially selecting individual ones of the channels of the plurality on the basis of externally provided selection signals including for each selection operating the selected transmitter for launching a test signal and timing the selected receiver channel responsiveness on the basis of externally provided timing signals, to provide a sequence of tests in accordance with the sequential selection;

processing signals as received through the sequentially operated receiver channels by a common circuit to obtain test data for each test and including in each instance of selection the providing for selective gating the common circuit including gates being adjustable as to timing for opening and closing on the basis of second timing signals constituting timing parameters, and the common circuit being further adjustable as to processing said signals as received, for the acquisition of particular amplitudes and transit times on the basis of additional operating parameters;

preparing the common circuit for each test by feeding the second timing signals and the signals representing the operating parameters to the common circuit, separately for each selection of a transmitter and receiver channel; and updating the signals representing timing and operation parameters to be used in a subsequent test on the basis of the test data information acquired as per the processing step during one or several tests preceeding the subsequent test.

2. In a method as in claim 1, and including the step of varying the step length.

3. In a method as in claim 1, and including the step of varying the sequence of channel selection.

4. The method as in claim 1, said preparing steps including storing the second timing signals and the signals representing operating parameters and feeding them to said common circuit in steps of the tests of the sequence as selected.

5. The method as in claim 1, including the steps of providing first selection signals to the transmitter and receiver channels in a particular sequence, and providing second selection signals to the channels for changing said sequence.

6. Method of automatically adjusting an ultrasonic system for nondestructively testing structural material, the system including at least one transmitter and receiver channel, operated for the conduction of sequential tests in individual steps on the material, each test step including launching an ultrasonic test pulse into the material and subsequently detecting by means of the receiver portion of the channel a response and return from the material, the system including means adjustable by electrical signals, for timing the launching of a test pulse, the means being adjusted by and in accordance with signals representing a first parameter;

the system further including means adjustable by electrical signals for timing responsiveness of the respective receiver portion of the channel or channels, the latter means being adjusted by and in accordance with signals representing a second parameter, the system further including an acquisition electronics having gating means adjustable by electrical signals for generating and timing looking windows for the response signal, the windows having specific beginnings and endings in accordance with electrical signals representing third parameters determining and timing these windows;

the acquisition unit further including response signal evaluating means adjustable by electrical signals for comparing the response signal and the occurrence of individual portions thereof as permitted to pass the windows with reference signals in accordance with and constituting forth parameters and producing test data for each said test, the steps comprising:

providing said signals constituting said first through fourth parameters as electrical signals, and feeding these signals to all said means, at least the signals constituting said third and fourth parameters being so fed separately for each test; and using the data as acquired in one or more of said tests to update the signals of at least one of the first through fourth parameters to generate a respective new parameter to be used as one of the parameters in a subsequent test and being so provided as per said providing step for the said subsequent test.

7. Method as in claim 6, wherein the acquisition step includes the detection of occurrence of one or more response signal portions in relation to particular transit time limits, said time limits being set in response to particular ones of and included in said reference signals, the using step including particularly changing one or more of the third signal parameters for said subsequent test on the basis of said detected occurrence, to shift the timing of at least one window relative to the timing of pulse launching for the said subsequent test.

8. Method of automatically adjusting a system for nondestructively, ultrasonic testing structural material, the system including a plurality of transmitter and receiver channels operated in steps for the conduction of a cyclically repeated sequence of individual test on the material, each such test involving one of the channels of the plurality, the test sequence including stepwise selecting the channels for the conduction of a test, each test including launching an ultrasonic test pulse into the material and subsequently detecting by means of the receiver portion of the selected channel a response and return from the material, the system including means for timing the launching of a test pulse, in accordance with first signals which when received by the means for timing set the timing of the launching as a first parameter;

further including means for timing responsiveness of the respective receiver portion of the selected channel in accordance with second signals which when received by the means for timing responsiveness set a beginning of responsiveness of the receiver portion as a second parameter for receiving return responses by the material, the system further including an acquisition electronics having gating means common to all channels and for generating looking windows for the response signal, the windows having specified beginnings and endings set in response to third signals constituting third parameters for determining and timing these windows;

the acquisition unit further including response signal evaluating means comparing the response signal and the occurrence of individual portions thereof with reference values, the reference values being determined by fourth signals received by the evaluating means as fourth parameters, said evaluating means producing test data for each said test, the steps comprising:

providing said first through fourth electrical signals, and feeding these signals to all said respective means, at least said third and fourth parameter signals being fed to the acquisition unit separately and anew for each test; and using the data as acquired in one or more of said tests to update at least one of the first through fourth parameters, to generate new signals as new parameter to be used as one of the parameters in a subsequent test and being so provided as per said providing step for the said subsequent test.

9. The method as in claim 8, and including the step of providing additional signals for selecting a channel of the channels for changing the sequence of tests.

* * * * *